(12) United States Patent
Oda

(10) Patent No.: US 8,027,525 B2
(45) Date of Patent: Sep. 27, 2011

(54) IMAGE DISPLAY METHOD AND IMAGE DISPLAY APPARATUS

(75) Inventor: Yasuharu Oda, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1021 days.

(21) Appl. No.: 11/867,375

(22) Filed: Oct. 4, 2007

(65) Prior Publication Data

US 2008/0112627 A1   May 15, 2008

(30) Foreign Application Priority Data

Nov. 9, 2006   (JP) .................................. 2006-304521

(51) Int. Cl.
G06K 9/00   (2006.01)
(52) U.S. Cl. .............................. 382/128; 128/922; 378/4
(58) Field of Classification Search .................. 382/100, 382/128, 131, 132; 378/4–27; 705/1.1, 2, 705/3; 128/922
See application file for complete search history.

(56) References Cited

U.S. PATENT DOCUMENTS

| | | | |
|---|---|---|---|
| 5,822,544 A * | 10/1998 | Chaco et al. ....................... 705/2 |
| 6,115,486 A * | 9/2000 | Cantoni ........................ 382/128 |
| 6,557,102 B1 | 4/2003 | Wong et al. | |
| 6,904,308 B2 | 6/2005 | Frisch et al. | |
| 7,688,995 B2 * | 3/2010 | Stoeckel ........................ 382/100 |
| 2004/0054657 A1 | 3/2004 | Takeyama | |
| 2005/0027570 A1 * | 2/2005 | Maier et al. ....................... 705/3 |
| 2005/0049461 A1 | 3/2005 | Honda et al. | |
| 2007/0036412 A1 * | 2/2007 | Stoeckel ........................ 382/128 |

FOREIGN PATENT DOCUMENTS

| | | |
|---|---|---|
| EP | 1 618 828 A1 | 1/2006 |
| JP | 2003-19111 | 1/2003 |

OTHER PUBLICATIONS

Zhou, X. O., et al., "Authenticity and Integrity of Digital Mammography Images", IEEE Transactions on Meclical Imaglng, ivol. 20, No. 8, Aug. 2001, pp. 784-791 (provided by applicant).*
Zhou, X. O., "Authenticity and Integrity of Digital Mammography Images", IEEE Transactions on Medical Imaging, vol. 20, No. 8, Aug. 2001, pp. 784-791

* cited by examiner

*Primary Examiner* — Anand Bhatnagar
(74) *Attorney, Agent, or Firm* — Scully, Scott, Murphy & Presser, P.C.

(57) ABSTRACT

An image display method and an image display apparatus realize prevention of misdiagnosis which is caused by corruption of a part of at least one type of information including identification information, information on a series of images, and diagnosis-report information. The image display method and the image display apparatus perform an operation using a predetermined hash function on patient information ID1, examination information ID2, a series of images I1 to In acquired by an intra-subject information acquiring apparatus to generate and add hash data h. Thereafter, the image display method and the image display apparatus, when using case 15a-1, perform an operation using a predetermined hash function to generate new hash data, compare each piece of the hash data h already added and newly generated hash data, and determine whether two pieces of hash data match with each other. Based on the result of determination, the use of the case data is canceled, or display of corrupted image is restricted, for example, so that the misdiagnosis is prevented.

16 Claims, 9 Drawing Sheets

IMAGE DISPLAY METHOD AND IMAGE DISPLAY APPARATUS

CROSS-REFERENCE TO RELATED APPLICATIONS

This application is based upon and claims the benefit of priority from Japanese Patent Application No. 2006-304521, filed Nov. 9, 2006, the entire contents of which are incorporated herein by reference.

BACKGROUND OF THE INVENTION

1. Field of the Invention

The present invention relates to an image display method and an image display apparatus according to which sameness of at least one type of information can be ensured and misdiagnosis and/or alteration can be prevented. The information includes identification information including patient information and examination information, information on a series of images acquired by an intra-subject information acquiring apparatus such as a capsule endoscoper and diagnosis-report information which is formulated and updated based on the above-listed information.

2. Description of the Related Art

In recent years, a swallowable capsule endoscope equipped with an imaging function and a radio communication function is proposed in a field of endoscope. Further, with the use of such a capsule endoscope, an intra-subject information acquiring system, which acquires images inside a subject, is being developed. After being swallowed by a subject from the mouth for an observation (examination), the capsule endoscope travels through body cavities, for example, internal organs such as a stomach and a small intestine following peristaltic movements thereof until naturally discharged from the subject. The capsule endoscope has a function of capturing images inside the body of the subject during the travel, for example, at intervals of 0.5 second.

During the travel inside the body of the subject, the capsule endoscope sequentially transmits images acquired through image-pickup to a receiver outside the subject via radio communication. The receiver has a radio communication function and a memory function, and sequentially stores the images transmitted from the capsule endoscope inside the body of the subject. The subject can move freely after swallowing the capsule endoscope until naturally discharging the same by carrying such a receiver. After the subject naturally discharges the capsule endoscope, a doctor or a nurse can make diagnosis of the subject by transferring the images stored in the memory of the receiver to an image display apparatus and displaying images of organs inside the body of the subject on the image display apparatus (see, for example, Japanese Patent Application Laid-Open No. 2003-19111).

Here, a series of images taken into the image display apparatus is stored together with patient information and examination information as case data. Further, a doctor formulates and adds a report to the case data. The report is updated as necessary.

Sometimes, however, the identification information such as the patient information and the examination information included in the case data is corrupted. Then, such corrupted patient information or the examination information can be recognized as information of a different patient or a different examination. The doctor may make diagnosis based on information of a different examination of a different patient, thereby making misdiagnosis.

Further, even when only a part of one image included in the case data is corrupted, the doctor may make diagnosis based on this single, corrupted image. Then, there is a possibility of misdiagnosis.

Still further, when the doctor uses a part of the series of images for formulating a diagnosis report, and a part of the image used in the diagnosis report is corrupted, the doctor may similarly make misdiagnosis. Still further, the diagnosis report itself can be altered.

SUMMARY OF THE INVENTION

An object of the present invention is to solve at least the above-described problems.

An image display method according to one aspect of the present invention includes generating first information by performing an operation using one of a predetermined function and an operation expression on at least one type of information of identification information including patient information and examination information, information on a series of images acquired by an intra-subject information acquiring apparatus, and diagnosis-report information formulated and updated based on the identification information and the information on a series of images, and by generating and adding first error detection information, generating second information by performing an operation using one of the predetermined function and the operation expression on at least one type of information to be output among the at least one type of information, and generating second error detection information, and determining whether the first error detection information and the second error detection information match with each other by comparing the first error detection information and the second error detection information.

An image display apparatus according to another aspect of the present invention includes a first information generating unit that performs an operation using one of a predetermined function and an operation expression on at least one type of information of identification information including patient information and examination information, information on a series of images acquired by an intra-subject information acquiring apparatus, and diagnosis-report information formulated and updated based on the identification information and the information on a series of images, and generates and adds first error detection information, a second information generating unit that performs an operation using one of the predetermined function and the operation expression on at least one type of information to be output among the at least one type of information, and generates second error detection information, and a determining unit that determines whether the first error detection information and the second error detection information match with each other by comparing the first error detection information and the second error detection information.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of an image display method and an image display apparatus according to the present invention will be described in detail below with reference to the accompanying drawings. It should be noted that the present invention is not limited to the embodiments.

Embodiment

Figure 1:
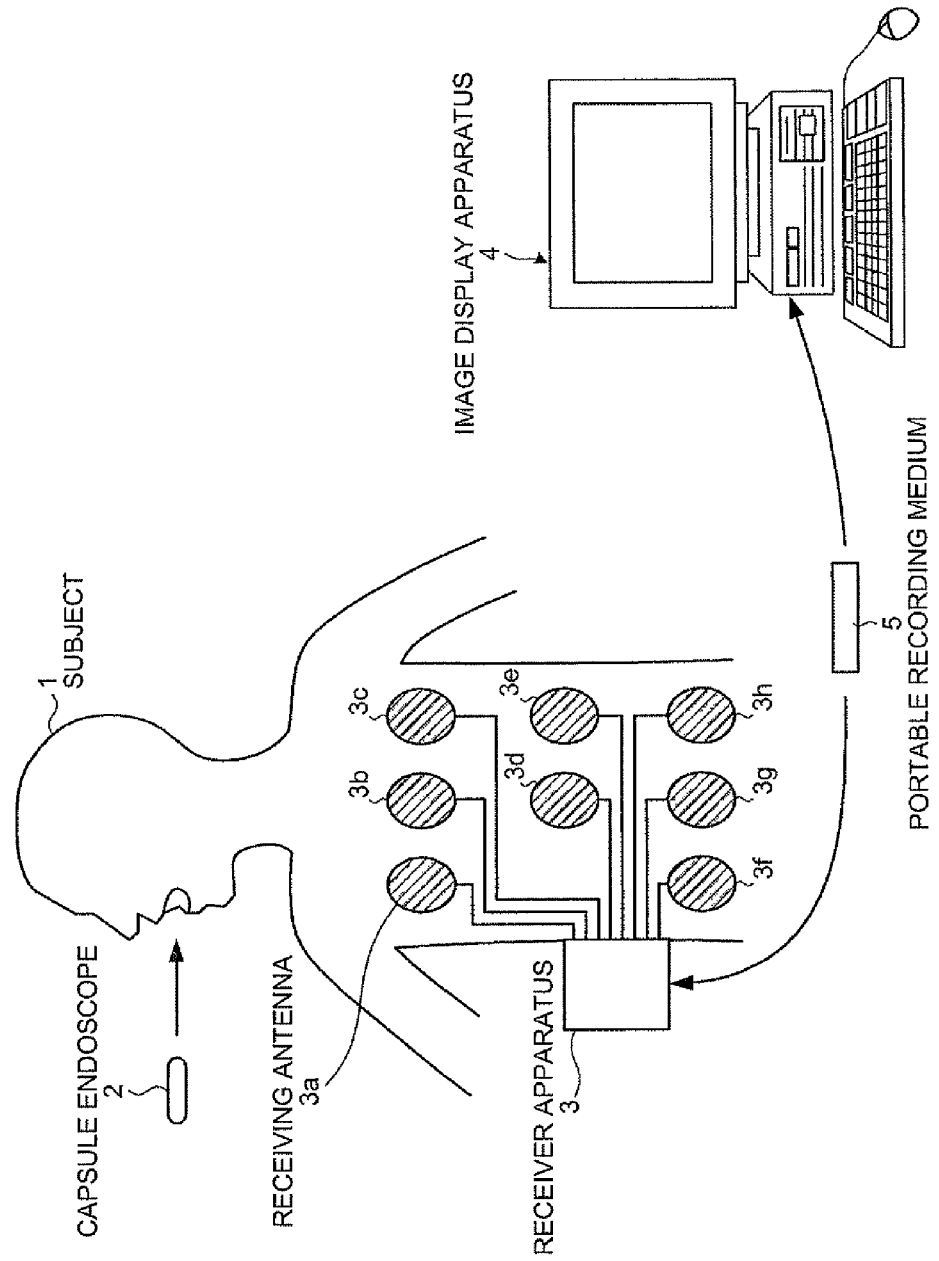
FIG. 1 is a schematic diagram of an exemplary configuration of an intra-subject information acquiring system including an image display apparatus according to an embodiment of the present invention.

FIG. 1 is a schematic diagram of an exemplary configuration of an intra-subject information acquiring system including an image display apparatus according to an embodiment of the present invention. As shown in FIG. 1, the intra-subject information acquiring system includes a capsule endoscope 2, a receiver apparatus 3, an image display apparatus 4, and a portable recording medium 5. The capsule endoscope 2 captures images of an inside of a subject 1 (hereinafter referred to as intra-subject images) while moving along a passage inside the subject 1. The receiver apparatus 3 receives radio signals sent from the capsule endoscope 2 and stores the images included in the received radio signals. The image display apparatus 4 displays the images stored in the image display apparatus 4, i.e., images captured by the capsule endoscope 2. The portable recording medium 5 serves to deliver information between the receiver apparatus 3 and the image display apparatus 4.

The capsule endoscope 2 serves to capture a group of intra-subject images inside the subject 1. The capsule endoscope 2 has an imaging function and a radio communication function which are equipped inside a capsule-type casing, and the capsule-type casing can be introduced into the internal organs of the subject 1. Specifically, after being swallowed from the mouth of the subject 1, the capsule endoscope 2 travels through the internal organs of the subject 1 following the peristaltic movements of the internal organs, for example. During the travel, the capsule endoscope 2 sequentially captures intra-subject images at predetermined intervals (e.g., 0.5 second). The capsule endoscope 2 sequentially transmits image signals including the intra-subject images of the subject 1 to the receiver apparatus 3 arranged outside the subject 1 by radio.

The receiver apparatus 3 serves to receive the group of intra-subject images of the inside of the subject 1 as captured by the capsule endoscope 2. Specifically, the receiver apparatus 3 has plural receiving antennas 3a to 3h, and is attached to (carried by) the subject 1 who swallows the capsule endoscope 2 into his/her internal organs. The receiver apparatus 3 sequentially receives the image signals transmitted from the capsule endoscope 2 inside the internal organ of the subject 1 by radio via the receiving antennas 3a to 3h, so as to acquire the group of intra-subject images captured by the capsule endoscope 2. The receiver apparatus 3 has the portable recording medium 5, and stores the group of intra-subject images of the subject 1 received from the capsule endoscope 2 into the portable recording medium 5.

The receiving antennas 3a to 3h are distributively arranged on a body surface of the subject 1 along the passage (i.e., along a digestive tract of the subject 1) of the capsule endoscope 2 inside the internal organ of the subject 1, for example, and are connected to the receiver apparatus 3. The receiving antennas 3a to 3h pick up the image signals sequentially transmitted from the capsule endoscope 2 in the internal organ of the subject 1 by radio, and sequentially transmit the picked-up image signals to the receiver apparatus 3. The receiving antennas 3a to 3h may be distributively arranged on a jacket or the like the subject 1 wears. The number of the receiving antennas provided for the pick-up of the image signals sent from the capsule endoscope 2 is not limited to eight, and any number of receiving antennas can be arranged as far as there is more than one receiving antenna per one subject 1.

The portable recording medium 5 is a recording medium such as a compact flash® that is portable, and serves for data delivery between the receiver apparatus 3 and the image display apparatus 4. Specifically, the portable recording medium 5 is attachable/detachable to/from the receiver apparatus 3 and the image display apparatus 4, and is configured to be able to output/record data when attached to the receiver apparatus 3 and the image display apparatus 4. When the portable recording medium 5 is attached to the receiver apparatus 3, the portable recording medium 5 records the group of intrasubject images, for example, of the subject 1 transmitted from the capsule endoscope 2 and received by the receiver apparatus 3. When the portable recording medium 5 is attached to the image display apparatus 4, the portable recording medium 5 transfers the recorded data such as the group of intra-subject images of the inside of the subject 1 to the image display apparatus 4.

Data recorded in the portable recording medium 5 is, for example, a group of intra-subject images of the subject 1, time information of each intra-subject image included in the group of intra-subject images (e.g., time of image pickup, time of reception), patient information of the subject 1, and examination information of the subject 1. The patient information of the subject 1 is identification information for identifying the subject. The patient information is, for example, name of the subject 1, patient ID, date and year of birth, sex, and age. The examination information of the subject 1 is identification information for identifying an endoscopic examination performed on the subject 1 (e.g., examination performed by inserting the capsule endoscope 2 inside an internal organ for observing the inside of the internal organ). The examination information is, for example, examination ID, and date of examination.

The image display apparatus 4 serves to display an image captured by the capsule endoscope 2, for example. Specifically, the image display apparatus 4 is configured like a workstation, for example, which takes in various types of information stored in the portable recording medium 5 while the portable recording medium 5 is attached to the receiver apparatus 3, thereby acquires various types of information such as images captured by the capsule endoscope 2, and displays images inside the subject 1 based on the acquired information. The image display apparatus 4 has an image display function for sequentially displaying each image included in the group of images of the subject 1r and further has a processing function for allowing the user such as a doctor and a nurse to observe (examine) the images inside the subject 1 to make diagnosis. The user can sequentially display the images inside the subject 1 on the image display apparatus 4 to observe (examine) a site in the subject 1, such as an esophagus, a stomach, a small intestine, and a large intestine, and make diagnosis.

Figure 2:
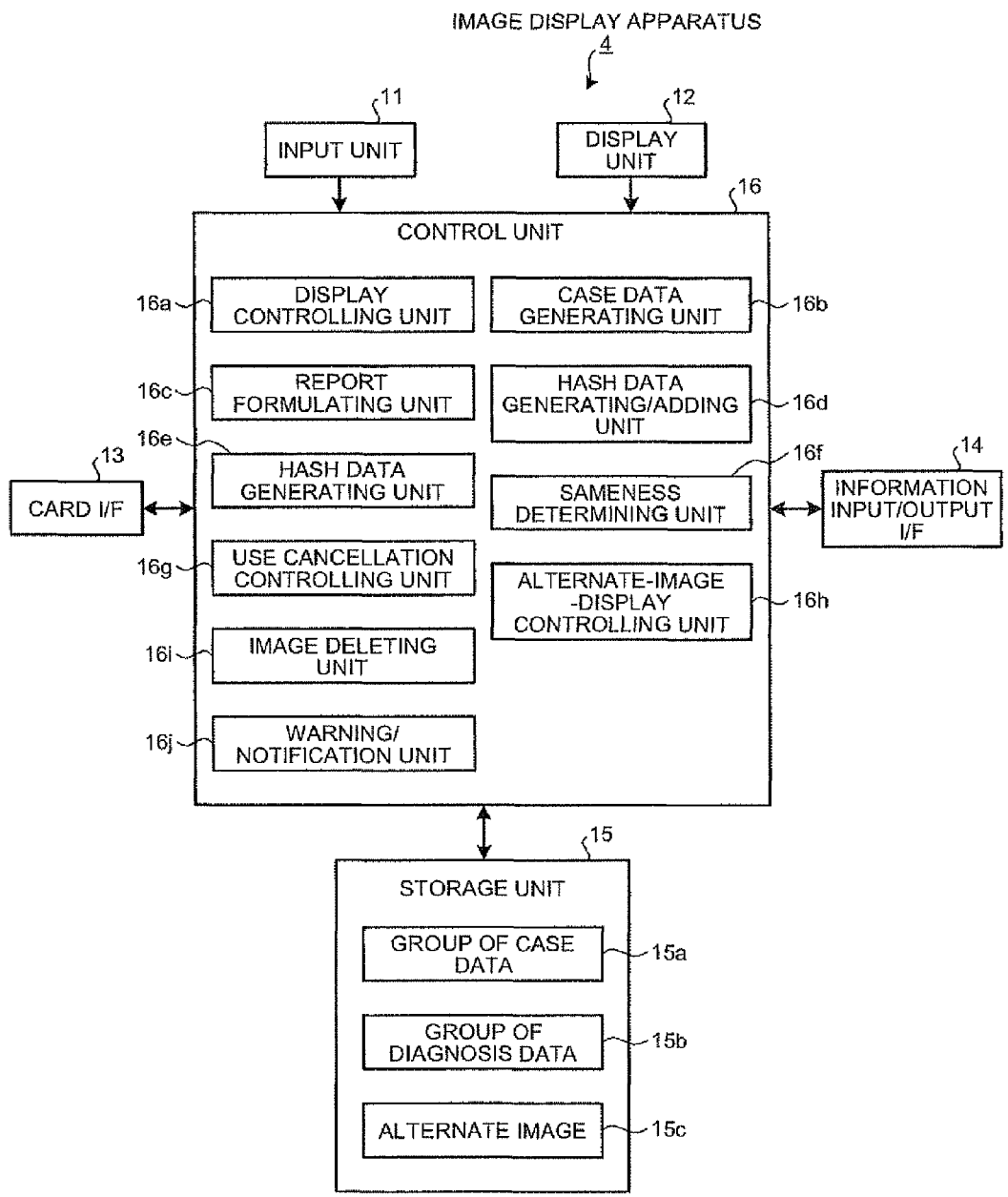
FIG. 2 is a schematic block diagram of an exemplary configuration of the image display apparatus according to the embodiment of the present invention.

A configuration of the image display apparatus 4 will be described. FIG. 2 is a schematic block diagram of an exemplary configuration of the image display apparatus 4 according to an embodiment of the present invention. As shown in FIG. 2, the image display apparatus 4 includes an input unit 11 that receives various types of information for an observation of an image(s) inside the subject 1, a display unit 12 that displays various types of information, such as an image(s) inside the subject 1 for the examination and the diagnosis of the subject 1 on a screen, and a card interface (I/F) 13 that serves to take in stored information, such as images inside the subject 1, accumulated in the portable recording medium 5. Further, the image display apparatus 4 includes an information input/output I/F 14 that serves to input/output various types of information such as an image(s) inside the subject 1 from/to an external computer, for example, a storage unit 15 that stores various types of information such as an image(s) of the subject 1, and a control unit 16 that controls the driving of each component of the image display apparatus 4.

The input unit 11 is configured with a keyboard and a mouse, for example. The user manipulates the input unit 11 to supply instruction information to give an instruction to the control unit 16 and to input patient information and/or examination information related to the subject 1 to the control unit 16. The patient information and the examination information are registered in the receiver apparatus 3 via the portable recording medium 5, for example, whereby the receiver apparatus 3 is initialized as a receiver apparatus for an examination of the subject 1 with the capsule endoscope. The patient information is, for example, name of the patient who is the subject 1, sex, date and year of birth, and patient identification information (ID information). The examination information is, for example, examination identification information such as date of examination, and a serial number of examination.

The display unit 12 is configured with various types of displays such as a Cathode Ray Tube (CRT) display, and a liquid crystal display. The display unit 12 displays various types of information for which the control unit 16 gives a display instruction. The display unit 12 displays various types of information for the observation and the diagnosis of the subject 1, such as the images of the subject 1 captured by the capsule endoscope 2. A specific example of a display screen of the display unit 12 will be described later.

The card I/F 13 serves to take in stored information in the portable recording medium 5. Specifically, the portable recording medium S is detachably inserted into the card I/F 13, which reads out the stored information in the portable recording medium 5, and simultaneously transfers the read-out information to the control unit 16. Further, the card I/F 13 writes in information for which the control unit 16 gives a writing instruction to the inserted portable recording medium 5. For example, the card I/F 13 writes in the patient information or the like into the portable recording medium 5.

The information input/output I/F 14 serves to perform input/output of various types of information between an external computer or a peripheral device and the image display apparatus 4, for example. Specifically, the information input/output I/F 14 is configured with a drive or the like, to which a portable recording medium such as a flexible disc (FD), a compact disc (CD), and Digital Versatile Disk (DVD) can be detachably inserted, and which performs reading processing or writing processing of various types of information on the inserted portable recording medium. Further, the information input/output I/F 14 is configured to be connectable to a peripheral device such as a printer via a predetermined cable. The information input/output I/F 14 writes in information, for which the control unit 16 gives a writing instruction, to the portable recording medium in the drive, or outputs information, for which the control unit 16 gives an output instruction, to a peripheral device such as a printer. Further, the information input/output I/F 14 reads out information, for which the control unit 16 gives a reading instruction, from the portable recording medium in the drive and transfers the read-out information to the control unit 16.

The storage unit 15 is configured with an information recording unit such as a random access memory (RAM), an electrically erasable programmable read-only memory (BEPROM), and a hard disk that can store and read out information. The storage unit 15 stores information, for which the control unit 16 gives a writing instruction, and transmits stored information for which the control unit 16 gives a reading instruction, to the control unit 16. The storage unit 15 stores a group of case data 15a of the subject, including a group of images of the subject, patient information, and examination information (e.g., date of examination and examination identification information), a group of diagnosis reports 15b which is a group of medical records of the subject formulated according to processing function of the image display apparatus 4, and an alternate image 15c which is displayed when an image to be displayed is corrupted in place of the corrupted image.

The control unit 16 controls the driving of each component of the image display apparatus 4, for example, the input unit 11, the display unit 12, the card I/F 13, the information input/output I/F 14, and the storage unit 15, and controls information input/output with these components. The control unit 16 includes a display controlling unit 16a that controls an operation of the display unit 12 to display various types of information, a case data generating unit 16b that generates each piece of case data of the group of case data 15a, a report formulating unit 16c that formulates a diagnosis report on which a result of diagnosis of the subject is described, a hash data generating/adding unit 16d that generates and adds hash data for each of the patient information, examination information, and the image included in each piece of the case data and each piece of the diagnosis report at a time of formulation of the case data by the case data generating unit 16b and at a time of formulation and update of the diagnosis report by the report formulating unit 16c, a hash data generating unit 16e that generates hash data for each of the patient information, the examination information, and the imager or the diagnosis report and the image cited in the diagnosis report at a time of use of the case data and the diagnosis report, a sameness determining unit 16f that compares the hash data added to the case data or the diagnosis report and the hash data generated by the hash data generating unit 16e, and determines sameness of the case data or the diagnosis report based on the value of hash data (i.e., whether the values of the hash data are the same or not), a use cancellation controlling unit 16g that controls cancellation of the use of the case data for which the hash data of the identification information such as the patient information and the examination information is determined not to be the same by the sameness determining unit 16f, an alternate-image-display controlling unit 16h that controls the display of the alternate image 15c which is displayed in place of an image, for which the hash data is determined not to be the same by the sameness determining unit 16f, in the case data, an image deleting unit 16i that deletes an image in the diagnosis report when the hash data for the image is determined not to be the same by the sameness determining unit 16f, and a warning/notification unit 16j that gives various types of warnings or notifications. The case data generating unit 16b adds hash data generated by the hash data generating/adding unit 16d, on generating the case data, and stores the data to which the hash data is added as the case data in the group of case data 15a.

Figure 3:
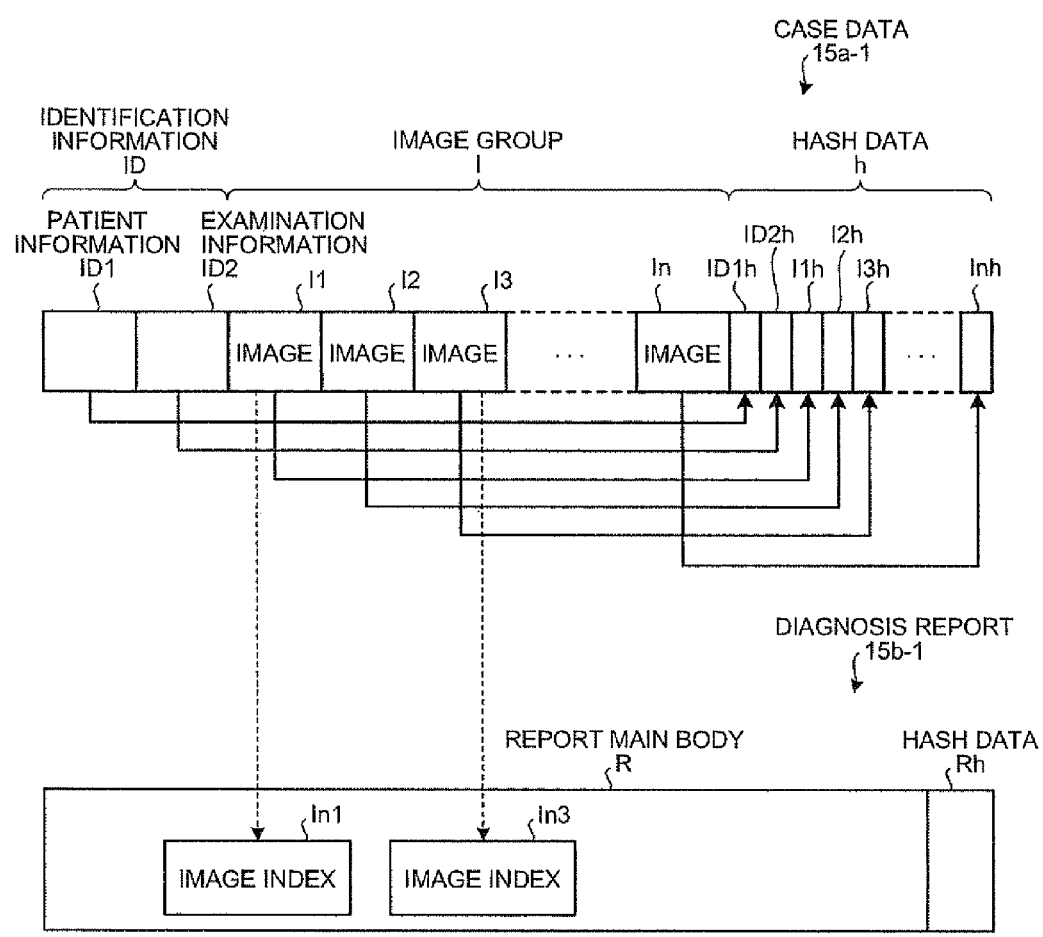
FIG. 3 shows a data structure of case data and diagnosis report.

FIG. 3 shows case data 15a-1 including hash data h which is generated and added by the hash data generating/adding unit 16d. As shown in FIG. 3, the case data 15a-1 includes identification information ID consisting of patient information ID1 and examination information ID2, a group of images I consisting of approximately 60thousands images I1 to In, and hash data h consisting of hash data ID1h of the patient information ID1, hash data ID2h of the examination information ID2, and hash data I1h to Inh of the respective images I1 to In. The hash data h is hash values calculated based on a predetermined hash function.

The diagnosis report 15b-1 is formulated in a form of an XML document. The diagnosis report 15b-1 includes a report main body R in which an image index designating an image cited in the case data 15a-1 is described, and hash data Rh corresponding to the report main body R. For example, as shown in FIG. 3, the diagnosis report 15b-1 includes an image index In1 referring to the image I1, and an image index In3 referring to the image I3. The hash data Rh is formulated and added at a time the diagnosis report main body R is initially described, and further updated at a time of update of the diagnosis report main body R.

Figure 4:
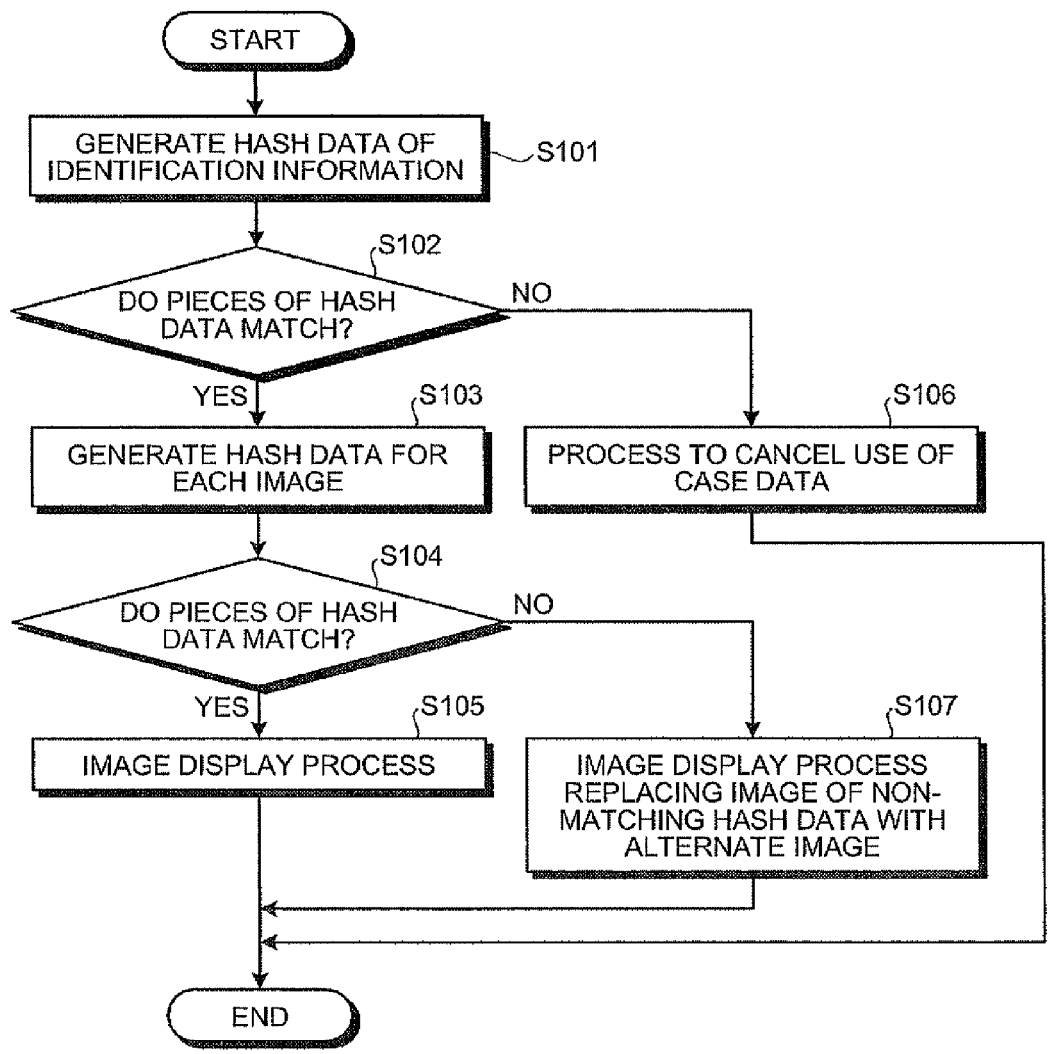
FIG. 4 is a flowchart of a misdiagnosis-prevention process performed on the case data.
Figure 5:
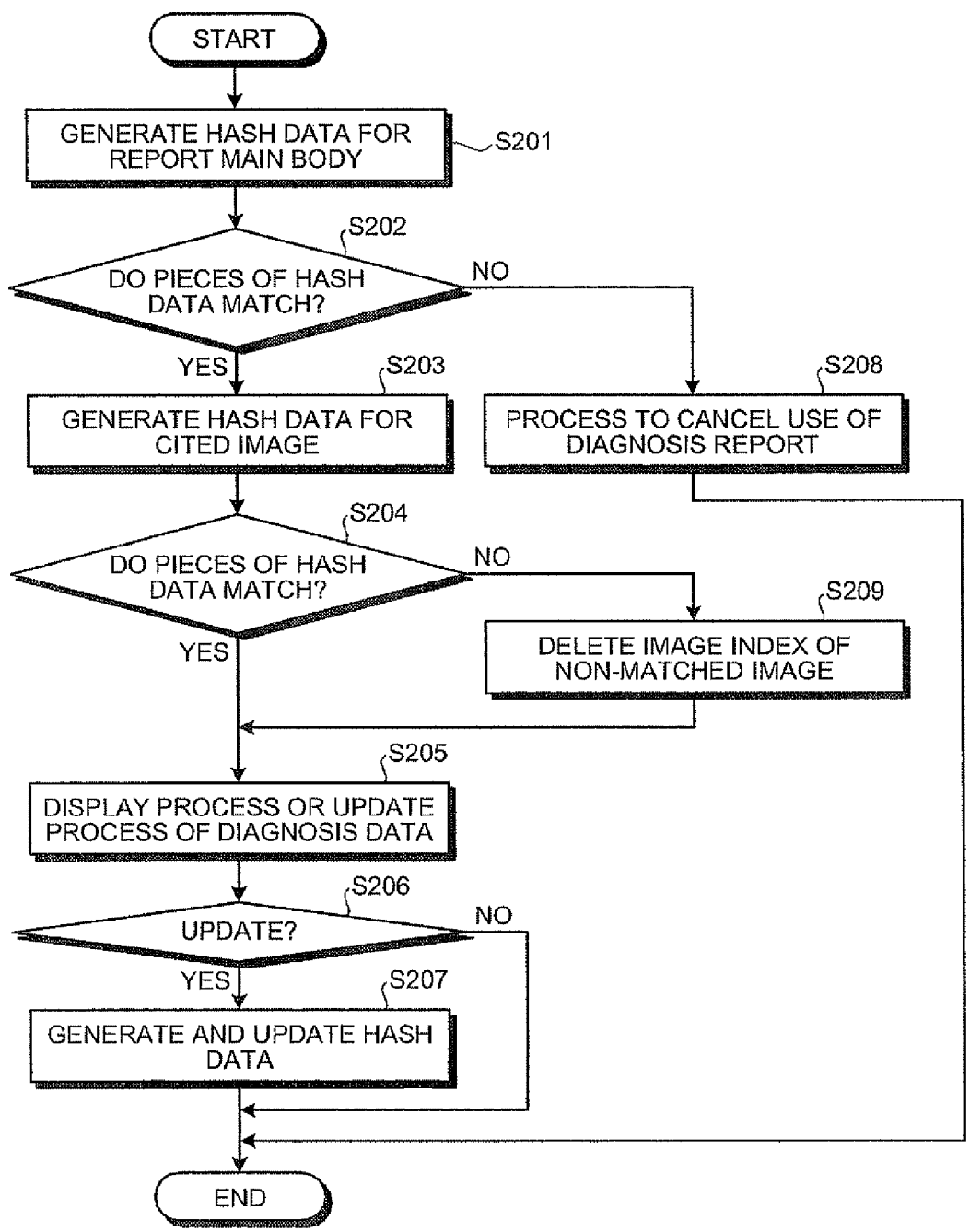
FIG. 5 is a flowchart of a misdiagnosis-prevention process performed on the diagnosis report.

Referring to flowcharts of FIGS. 4 and 5, a misdiagnosis-prevention process performed by the control unit 16 will be described. In FIG. 4, the misdiagnosis-prevention process performed on the case data 15a-1 is shown. First, the hash data generating unit 16e newly generates hash data for the identification information ID at a time of use of the case data 15a-1 (step S301). Thereafter, the sameness determining unit 16f determines whether the newly-generated hash data coincide with existing hash data ID1h and ID2h (step S102).

When the pieces of the hash data of the identification information ID match with each other (Yes in step S102), the hash data generating unit ie further generates hash data for each image included in the image group I (step S103). Thereafter, the sameness determining unit 16f determines whether all pieces of the newly-generated hash data coincide with the corresponding pieces of existing hash data I1h to Inh of the images (step S104). When all pieces of the hash data coincide with each other (Yes in step S104), the display controlling unit 16a executes a display process of each image (step S105) assuming that the case data is not corrupted or altered. Thus, a main process ends.

On the other hand, when there is hash data of the identification information ID which does not coincide (No in step S102), the use cancellation controlling unit 16g performs a cancellation process to stop the use of the case data 15a-1 (step S106), and ends the main process. In the cancellation process of the use cancellation controlling unit 16g, the warning/notification unit 16j displays a warning to notify that the use of the case data 15a-1 is not currently permitted and a process to prohibit the access is performed when there is an access to the case data 15a-1. Thus, the diagnosis is prevented from being made based on the patient information ID1, the examination information ID2, and each image of the image group I, not corresponding with each other, whereby misdiagnosis is prevented. In other words, patient mix-up can be prevented.

When pieces of hash data of an image in the image group I do not coincide with each other (No in step S104), the alternate-image-display controlling unit 16h replaces an image corresponding to the non-matched hash data with the alternate image 15c, performs a display process of each image by the display controlling unit 16a (step S107), and the main process ends. The alternate image 15c is, for example, a triangular warning symbol, or an image marked out in a single color. The alternate image is employed because it is inefficient to cancel the use of all images when there is an image partially corrupted or altered, and the prevention of misdiagnosis can be realized with the use of the alternate image.

A misdiagnosis-prevention process on the diagnosis report will be described with reference to the flowchart of FIG. 5. In FIG. 5, the hash data generating unit 16e generates new hash data for the report main body R at a time of formulation or update of the diagnosis report (step S201). Thereafter, it is determined whether the newly-generated hash data coincides with the existing hash data Rh of the report main body R (step S202). When the newly-generated hash data coincides with the existing hash data of the report main body R (Yes in step 3202), the hash data generating unit 16e further generates hash data for an image in the case data 15a-1 indicated by the image index in the report main body R (step S203). Thereafter, it is determined whether the newly-generated hash data coincides with the existing hash data of the image (step S204). When the hash data of the cited image coincides (Yes in step S204), a display process or an update process of the diagnosis report 15b-1 is performed (step S205). Thereafter, the control unit 16 determines whether the report formulating unit 16c updates the diagnosis report 15b-1 or not (step S206). When the update process of the diagnosis report has been performed (Yes in step S206), the hash data generating/adding unit 16d generates and adds (updates) the hash data for the report main body of the updated diagnosis report (step 3207) and ends the main process. On the other hand, when the update process of the diagnosis report has not been performed (No in step S206), the main process immediately ends.

On the other hand, when the hash data of the report main body R does not coincide (No in step S202), the use cancellation controlling unit 16g performs a cancellation process to cancel the use of the diagnosis report 15b-1 (step S208) similarly to the process based on the identification information ID, and ends the main process. Thus, the misdiagnosis and the alternation can be prevented from being made from the corruption of data in the diagnosis report.

Further, when the hash data of the cited image does not coincide (No in step S204), the image deleting unit 16i deletes the non-matched image index (step S209), deletes the image in the diagnosis report 15b-1, and ends the main process. The deletion of the image index allows for the prevention of misdiagnosis at the time of formulation or update of the diagnosis report.

Modification of Embodiment

A modification of the embodiment will be described. In the image display apparatus shown in FIG. 2, the alternate-image-display controlling unit 16h makes the alternate image 15c displayed in place of the image for which the hash data does not match. In the modification, the image for which the hash data does not match is skipped during display.

Figure 6:
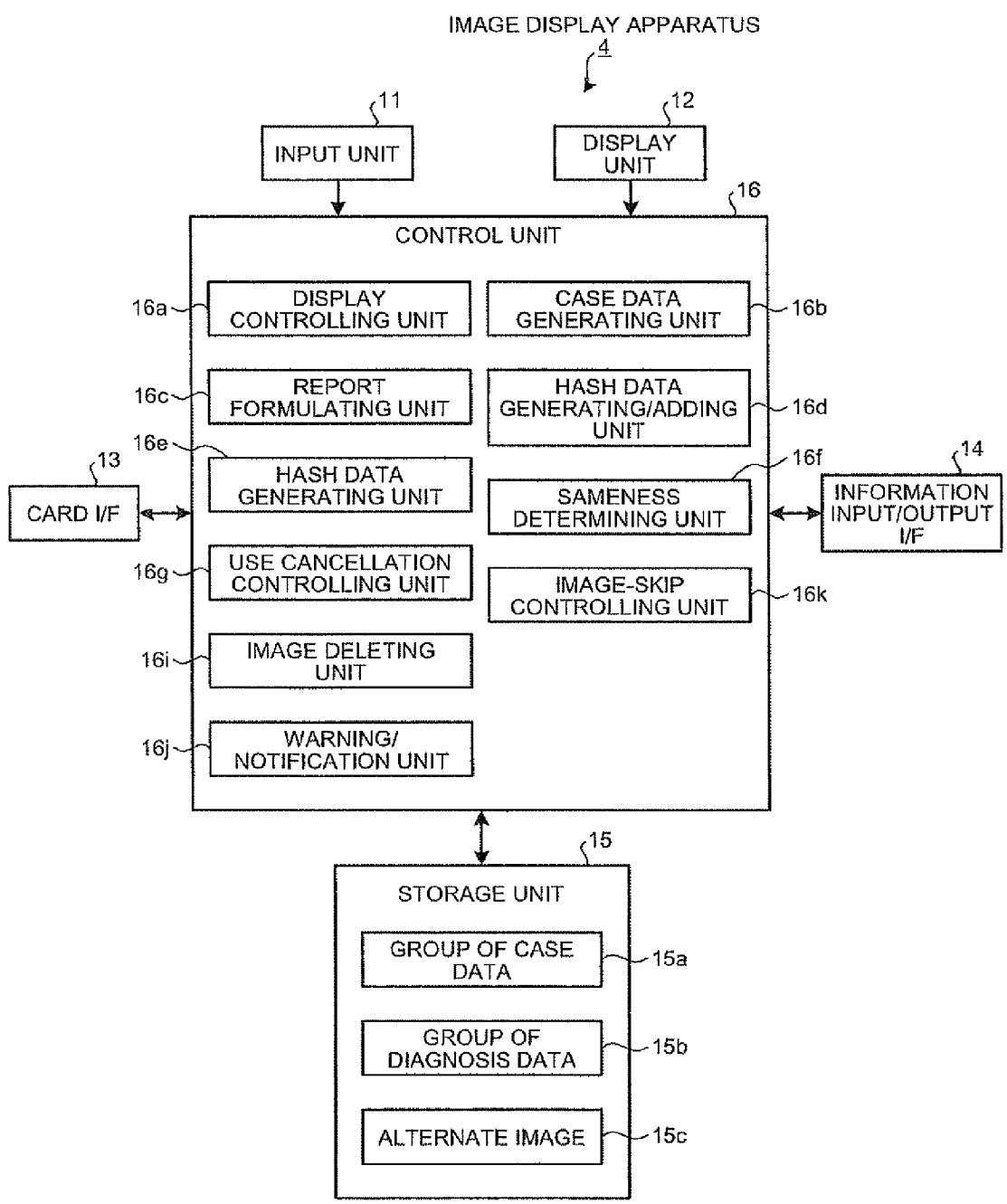
FIG. 6 is a schematic block diagram of an exemplary configuration of an image display apparatus according to a modification of the embodiment of the present invention.

FIG. 6 is a block diagram of a configuration of an image display apparatus according to the modification of the embodiment of the present invention. As shown in FIG. 6, the image display apparatus is provided with an image-skip controlling unit 16k in place of the alternate-image-display controlling unit 16h shown in FIG. 1. The image-skip controlling unit 16k controls the display controlling unit 16a so that, when there is an image for which the hash data does not match, a series of images are displayed while the non-matched image is skipped.

Figure 7:
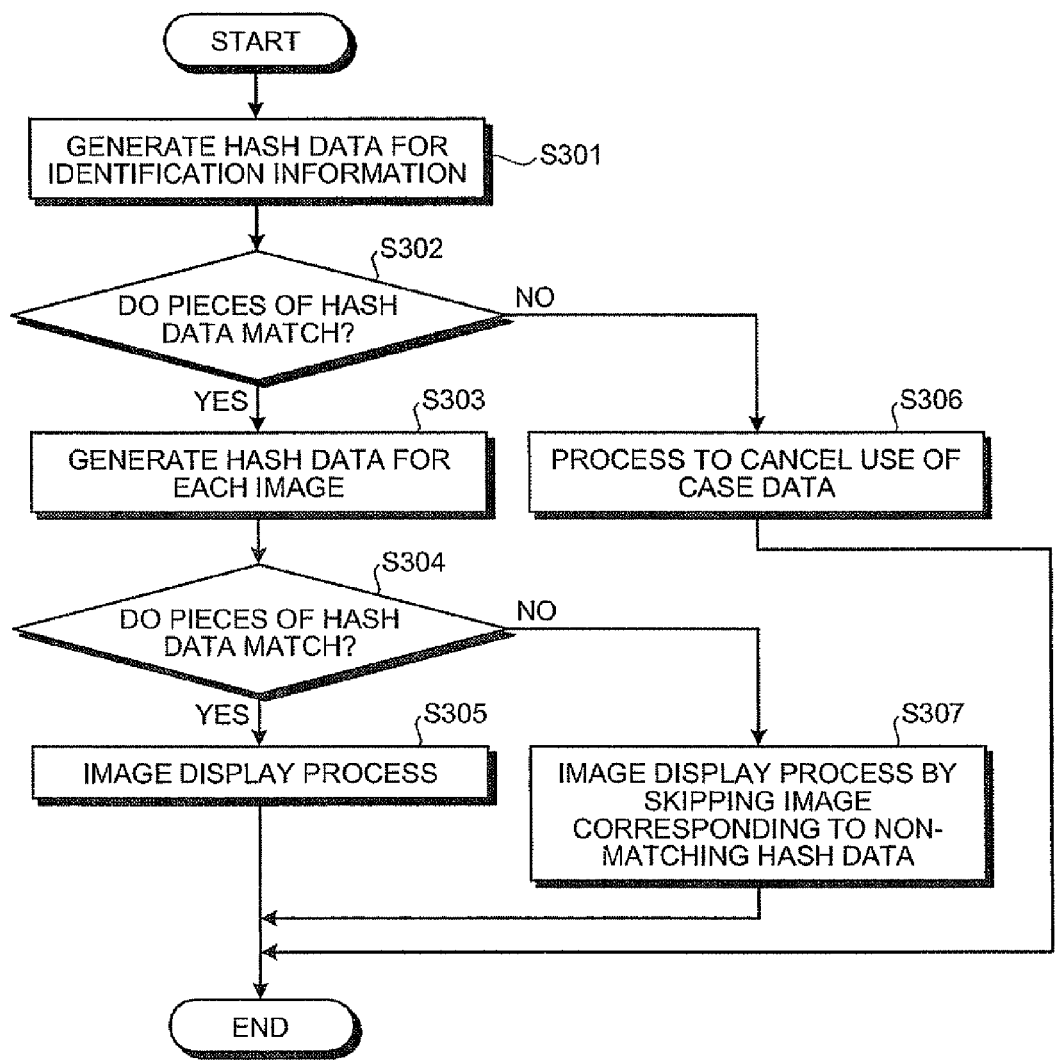
FIG. 7 is a flowchart of a misdiagnosis-prevention process performed on the case data according to the modification of the embodiment of the present invention.

FIG. 7 is a flowchart of a misdiagnosis-prevention process of images in the image display apparatus according to the modification. In FIG. 7, processes in steps S301 to S306 are the same as those in the steps S101 to S106 shown in FIG. 4. In the modification, the image-skip controlling unit 16k performs a process to display a series of images while skipping the image corresponding to the non-matched hash data in a process (step S307) replacing the process of step S107. Thus, a corrupted image and an altered image are not displayed, whereby the misdiagnosis can be prevented.

Figure 8:
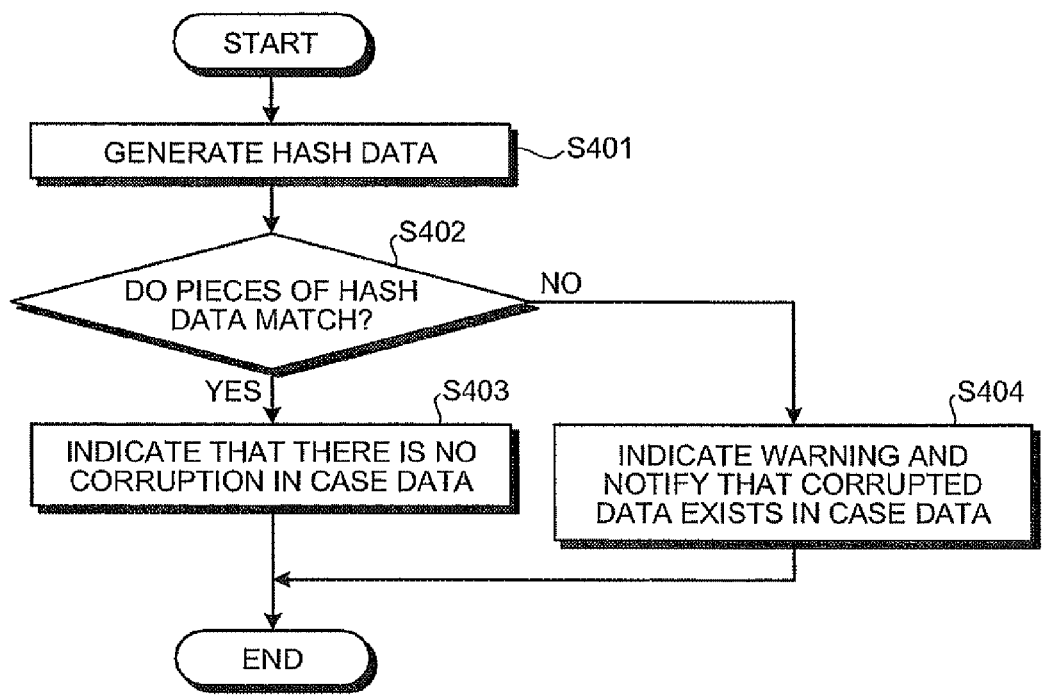
FIG. 8 is a flowchart of a processing procedure for detecting whether the case data is corrupted or not.

FIG. 8 is a flowchart of a process procedure of another modification of the embodiment. As described above, the embodiment realizes the misdiagnosis-prevention process using the hash data attached to the case data. When it is known in advance that it is highly likely that the case data is corrupted, it is preferable that the pertinent case data can be checked for corruption immediately. In the another modification, the corruption of the case data can be detected at any time.

As shown in FIG. 8, the hash data generating unit 16e first generates hash data for all of the case data, i.e., for the patient information ID1, the examination information IDS, and each of the images I to In (step S401). Thereafter, the sameness determining unit 16f determines whether all pieces of the hash data match or not (step S402). When all pieces of the hash data match (Yes in step S402), the warning/notification unit 16j indicates that there is no corruption in the case data 15a-1 (step S403), and the main process ends.

On the other hand, when all pieces of the hash data do not match (No in step S402), the warning/notification unit 16j performs a process to indicate a warning and give notification to notify that there is data corruption in the case data 15a-1 (step S404), and the main process ends. Thus, the user can know whether there is corruption in the case data or not at any time.

The report formulating unit c controls so that the formulation of the image index is prohibited for the images for which the alternate image 15c is applied by the alternate-image-display controlling unit Ih or which is skipped by the image-skip controlling unit 16k.

In the above embodiment, the hash data is generated and added to all data elements constituting the case data, i.e., the patient information, the examination information, and each of the images. Such operation is not a limiting example, however, and the hash data may be generated and added to one or more of the data elements.

The hash data generated by the hash data generating/adding unit 16d can be referred to as first error detection information, whereas the hash data generated by the hash data generating unit 16e can be referred to as second error detection information. The hash data is described as an example covered by the concept of the error detection information. Therefore, a simple check sum may be employed in place of the hash function. Alternatively, a cyclic code such as CRC code, parity code, or more widely, a block code may be employed. As far as uniquely-determined data, such as hash data, can be generated, any of these functions or operation expressions can be employed.

The use of the hash data prevents the misdiagnosis as described above, and moreover, alteration can be prevented even more securely when an algorithm using a predetermined hash function is prevented from being made public. Therefore, though there can be difference in the strength of encryption, in addition to the use of the hash function, by applying an algorithm using an arbitrary error detection code and keeping an algorithm of generation of error detection information from public, the alteration prevention can be achieved.

Figure 9:
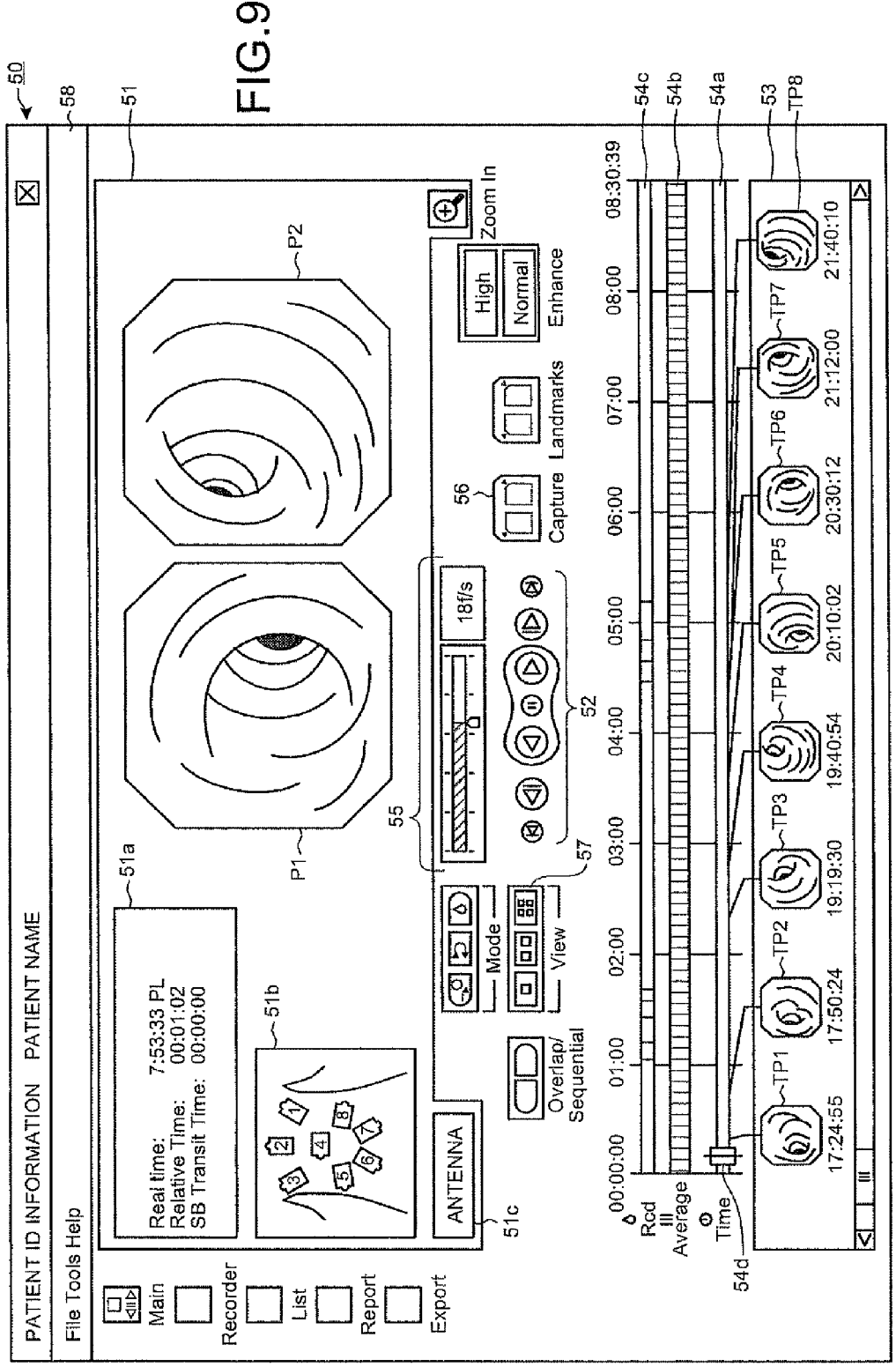
FIG. 9 is a schematic diagram of a specific example of a display screen of a display unit.

One specific example of a display screen (display mode) of the display unit 12 described above will be described. FIG. 9 is a schematic diagram of one specific example of the display screen of the display unit 12. The display controlling unit 16a makes the display unit 12 display a window 50 as shown in FIG. 9 when the control unit 16 performs a predetermined log-in process. The window 50 has a Graphical User Interface (GUI) for displaying a group of intra-subject images of the subject 1 to enable the observation of the inside of the internal organs of the subject 1. The display controlling unit 16a controls a display condition of the window 50.

Specifically, as shown in FIG. 9, the window 50 has a main image display portion 51 for displaying a group of intra-subject images of the subject 1, a group of display operation icons 52 for performing various display operations to display the group of intra-subject images in the main image display portion 51, and a sub-image display portion 53 for displaying a thumbnail image corresponding to a desired intra-subject image selected from the group of intra-subject images of the subject 1. Further, the window 50 has a time bar 54a for indicating a temporal position of each intra-subject image included in the group of intra-subject images of the subject 1, an average-color bar 54b for indicating an average color of the group of intra-subject images included in each temporal position indicated by the time bar 54a, a bleeding bar 54c for indicating a temporal position of one or more bleeding images included in the group of intra-subject images of the subject 1, and a slider 54d for indicating a temporal position of a currently-displayed image shown in the main image display portion 51 of temporal positions indicated by the time bar 54a. Further, the window 50 has a frame-rate indicating portion 55 for indicating a frame rate of the group of intra-subject images shown in the main image display portion 51, a registration indicating portion 56 for indicating information on whether it is an intra-subject image for which the thumbnail image has been registered or not, a display number setting portion 57 for setting a number of intra-subject images to be collectively shown in the main image display portion 51, and a menu bar 58 for indicating various menus such as a file menu, a tool menu, and a help menu.

The main image display portion 51 sequentially displays the group of intra-subject images of the subject 1 in response to display operations of the group of display operation icons 52 (such as "playback", "fast-forward", and "suspend"). The main image display portion 51 displays the intra-subject images of the number set in the display number setting portion 57 at one time. For example, when the display number setting portion 57 indicates the set number of intra-subject images as "2", the main image display portion 51 sequentially displays two images out of the group of intra-subject images of the subject 1 at one time as illustrated by intra-subject images P1 and P2 of FIG. 9. The number of intra-subject images set in the display number setting portion 57 is, for example, "one", "two", or "four."

The main image display portion 51 has a time information display portion 51*a* for indicating time information of the currently-displayed intra-subject image (i.e., currently displayed image), and an antenna position information display portion 51*b*. The time information display portion 51*a* displays time information corresponding to the currently-displayed image of the main image display portion 51 as illustrated by the intra-subject images P1 and P2 of FIG. 9. For example, the time information display portion 51*a* displays time of image pickup of the currently-displayed image, relative time from a header image (i.e., an intra-subject image which is captured at earliest time point) in the group of intra-subject images of the subject 1.

The antenna position information display portion 51*b* displays a position of the receiving antenna which captures the currently-displayed image at a highest received-magnetic-field strength among the receiving antennas 3*a* to 3*h* of the receiver apparatus 3 (see FIG. 1) receiving the currently-displayed image. The antenna position information display portion 51*b* can display a presumed position of the capsule endoscope 2 at a time of the image pickup of the currently-displayed image by showing such antenna position information. A function of information display of the antenna position information display portion 51*b* can be switched between an effective state and an ineffective state through the clicking of a display setting icon 51*c*.

The sub-image display portion 53 displays one or more thumbnail images corresponding to one or more images of the group of intra-subject images selected from the group of intra-subject images of the subject 1 shown in the main image display portion 51. Specifically, whenever the user selects (clicks) a desired intra-subject image from the group of intra-subject images sequentially displayed in the main image display portion 51 through the manipulation of the input unit 11, a thumbnail image corresponding to the selected desired intra-subject image is registered. The sub-image display portion 53 sequentially adds a registered thumbnail image (thumbnail images TP1 to TP8, for example) to the display. Further, the sub-image display portion 53 has a scrolling function, and a desired number of thumbnail images can be displayed other than eight thumbnail images TP1 to TP8.

The time bar 54*a* indicates a temporal position of each intra-subject image of the group of intra-subject images of the subject 1 shown in the main image display portion 51. The slider 54*d* moves on the time bar 54*a* according to the time information of the currently-displayed image in the main image display portion 51, so as to indicate a temporal position corresponding to the currently-displayed image on the time bar 54*a*. The average-color bar 54*b* and the bleeding bar 54*c* are arranged along the time axis of the time bar 54*a*. The average-color bar 54*b* indicates an average color of plural intra-subject images present at each temporal position on the time bar 54*a* for each temporal position. The bleeding bar 54*c* indicates a temporal position of one or more bleeding images using a red marker, for example, when the group of intra-subject images of the subject 1 includes one or more bleeding images (i.e., intra-subject image in which an image of a bleeding portion is captured).

The frame rate display portion 55 sequentially displays a display speed (frame rate) of sequential display of the group of intra-subject images of the subject 1 in the main image display portion 51 for each intra-subject image. Specifically, the frame rate display portion 55 sequentially displays a frame rate of the currently-displayed image in the main image display portion 51 every time one or more intra-subject images is displayed in the main image display portion 51. The frame rate display portion 55 displays a level of the frame rate of the currently-displayed image in the main image display portion 51 by a position on a bar, and by a numerical value as shown in FIG. 9, for example. The user can easily and visually recognize whether the frame rate of one or more intra-subject images displayed in the main image display portion 51 is set to a desirable level or not by checking the display of the bar and the numerical value of the frame rate display portion 55.

The registration display portion 56 displays information on whether a thumbnail image corresponding to the currently-displayed image shown in the main image display portion 51 has already been registered or not. Specifically, the registration display portion 56 displays predetermined marks (such as a triangular mark shown in FIG. 9) of the same number as the number of the intra-subject images concurrently displayed in the main image display portion 51, and indicates whether the thumbnail image corresponding to the currently-displayed image has been registered or not by changing a display mode (e.g., a color) of the predetermined mark. For example, in FIG. 9, if the registration display portion 56 turns the color of the left-side triangular mark into blue, and the color of the right-side triangular mark into white, it means that, of the currently-displayed images in the main image display portion 51, namely the intra-subject images P1 and P2, the left-side intra-subject image P1 is an intra-subject image for which a thumbnail image has already been registered, and the right-side intra-subject image P2 is an intra-subject image for which the thumbnail image has not been registered.

It may be possible to display a color bar before the display process of each image of the case data 15*a*-1 is performed, so as to check whether the original image can be correctly reproduced or not. The color bar represents a color range in a bar-like region of predetermined plural colors on the display screen. Thus, the misdiagnosis can be further prevented.

Further, the setting of a minimum screen resolution and a minimum color resolution of the employed image display apparatus may be checked for the correct reproduction of the currently-displayed image. For example, if a spec guaranteeing the display of an image to be displayed is 32-bit display in XGA (1024×768 pixels), the control unit 16 determines whether the image display apparatus is set to a screen resolution equal to or exceeding XGA and color resolution equal to or more than 32 bits. If not, the control unit 16 may display a warning/notification to recommend the setting to the screen resolution equal to or more than XGA and the color resolution equal to or more than 32 bits. Further, the control unit 16 may cancel the display process when the screen resolution and the color resolution are not set higher than the designated values. Such warning/notification and display cancellation control allow for even more secure misdiagnosis prevention.

In the above, when the sameness determining unit 16*f* determines that the hash data of the image within the diagnosis report is not same, the image deleting unit 16*i* deletes the pertinent image for which the hash data does not match from the diagnosis report. Alternatively, however, when the sameness determining unit 16*f* determines that the hash data of the image within the case data is not same, the image for which the hash data does not match may be deleted from the case data. Then, the display controlling unit 16*a* makes the display unit 12 display images other than the image determined to have non-matched hash data on displaying a series of images (e.g., image group I) in the subject included in the case data.

Further, in the above, one or more images included in the diagnosis report 15*b*-1 within the group of diagnosis reports 15*b* for which the sameness determining unit 16*f* determines that the hash data is not same is deleted from the diagnosis report 15*b*-1. Alternatively, however, an alternate image (e.g., alternate image 15c) which indicates non-matching may be displayed by the display unit 12 in place of the image for which the hash data does not match. Then, instead of the process in step S209, a process may be performed to change an image index of the image for which the hash data does not match with an image index of the alternate image 15c. Thus, when the hash data is determined to be non-identical, the alternate-image-display controlling unit 16h makes the display unit 12 display the alternate image 15c in place of the image for which the hash data is determined not to be the same on displaying the diagnosis report 15b-1.

Further, a warning/notification to notify that there is data corruption in the case data or the diagnosis report may be sent only once at a time when the hash data is first determined to be non-identical for one piece of case data or diagnosis report, or may be sent every time the hash data is determined to be non-identical.

In the image display method and the image display apparatus according to the present invention, an operation is performed with the use of one of a predetermined function and an operation expression on at least one type of information of identification information including patient information and examination information, information on a series of images acquired by an intra-subject information acquiring apparatus, and diagnosis-report information formulated and updated based on the identification information and the information on a series of images, so as to generate and add first error detection information. Thereafter, an operation is performed with the use of one of the predetermined function and the operation expression on at least one type of information to be output among the at least one type of information, so as to generate second error detection information, and the first error detection information and the second error detection information are compared and it is determined whether they match with each other or not. Thus, based on the result of determination, a process can be performed to prohibit the output of corrupted information and/or altered information included in the at least one type of information to be output, whereby misdiagnosis and alteration can be prevented.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

As can be seen from the foregoing, the image display method and the image display apparatus according to the present invention are useful for an examination of an inside of a subject through observation of each image captured in an inside of an internal organ of the subject such as a patient, and more particularly, are suitable for an image display method and an image display apparatus which can prevent misdiagnosis caused by the corruption of at least one type of information of identification information of the subject, information on a series of images, and diagnosis-report information.

What is claimed is:

1. An image display method comprising:
    generating first information by performing an operation using one of a predetermined function and an operation expression on at least one type of information of identification information including patient information and examination information, information on a series of images acquired by an intra-subject information acquiring apparatus, and diagnosis-report information formulated and updated based on the identification information and the information on a series of images, and by generating and adding first error detection information;
    generating second information by performing an operation using one of the predetermined function and the operation expression on at least one type of information to be output among the at least one type of information, and generating second error detection information;
    determining whether the first error detection information and the second error detection information match with each other by comparing the first error detection information and the second error detection information; and
    when the determining determines that the first error detection information and the second error detection information do not match with each other, performing a predetermined process in an image for which non-matching is determined and displaying the image.

2. The image display method according to claim 1, wherein the performing includes prohibiting a use of the at least one type of information to be output when non-matching is determined in the determining.

3. The image display method according to claim 1, wherein the performing includes displaying an alternate image which indicates non-matching in place of the image for which the non-matching is determined in the determining when the at least one type of information to be output is the information on a series of images.

4. The image display method according to claim 1, wherein the performing includes displaying a series of images by skipping the image for which the non-matching is determined in the determining when the at least one type of information to be output is the information on a series of images.

5. The image display method according to claim 1, wherein the performing includes displaying, when the at least one type of information to be output is the information on a series of images, images in the series of images other than the image for which the non-matching is determined in the determining by deleting the image for which the non-matching is determined.

6. The image display method according to claim 1, wherein
    the generating the second information includes generating the second error detection information by including an image included in the diagnosis-report information when the at least one type of information to be output is the diagnosis-report information, and the-performing includes
    deleting the image included in the diagnosis-report information from the diagnosis-report information and giving a warning/notification on displaying the diagnosis-report information, when the image included in the diagnosis-report information is determined to be non-matching in the determining.

7. The image display method according to claim 1, wherein
    the generating the second information includes generating the second error detection information by including an image included in the diagnosis-report information when the at least one type of information to be output is the diagnosis-report information, and the performing includes
    displaying an alternate image indicating non-matching in place of the image included in the diagnosis-report information on displaying the diagnosis-report information, when the image included in the diagnosis-report information is determined to be non-matching in the determining.

8. The image display method according to claim 1, further comprising notifying that corrupted information exists in the at least one type of information to be output, when non-matching is determined in the determining.

9. The image display method according to claim 1, wherein the predetermined function is a hash function.

10. An image display apparatus comprising:
- a first information generating unit that performs an operation using one of a predetermined function and an operation expression on at least one type of information of identification information including patient information and examination information, information on a series of images acquired by an intra-subject information acquiring apparatus, and diagnosis-report information formulated and updated based on the identification information and the information on a series of images, and generates and adds first error detection information;
- a second information generating unit that performs an operation using one of the predetermined function and the operation expression on at least one type of information to be output among the at least one type of information, and generates second error detection information;
- a determining unit that determines whether the first error detection information and the second error detection information match with each other by comparing the first error detection information and the second error detection information; and
- when the determining unit determines that the first error detection information and the second error detection information do not match with each other, a control unit performs a predetermined process on an image for which non-matching is determined and a display unit displays the image.

11. The image display apparatus according to claim 10 wherein the control unit includes a use prohibiting unit that prohibits a use of the at least one type of information to be output when non-matching is determined by the determining unit.

12. The image display apparatus according to claim 10 wherein the control unit includes an alternate-image-display unit that displays an alternate image which indicates non-matching in place of the image for which the non-matching is determined by the determining unit when the at least one type of information to be output is the information on a series of images.

13. The image display apparatus according to claim 10 wherein the control unit includes a skip-display unit that displays a series of images by skipping the image for which the non-matching is determined by the determining unit when the at least one type of information to be output is the information on a series of images.

14. The image display apparatus according to claim 10 wherein
- the second information generating unit generates the second error detection information by including an image included in the diagnosis-report information when the at least one type of information to be output is the diagnosis-report information, and the control unit further includes
- a deleting unit that deletes the image included in the diagnosis-report information from the diagnosis-report information and gives a warning/notification on displaying the diagnosis-report information, when the image included in the diagnosis-report information is determined to be non-matching by the determining unit.

15. The image display apparatus according to claim 10 further comprising
- a notifying unit that notifies that corrupted information exists in the at least one type of information to be output, when non-matching is determined by the determining unit.

16. The image display apparatus according to claim 10 wherein the predetermined function is a hash function.

* * * * *